United States Patent [19]

Iacovelli

[11] Patent Number: 5,350,391
[45] Date of Patent: Sep. 27, 1994

[54] LAPAROSCOPIC INSTRUMENTS

[76] Inventor: Benedetto Iacovelli, 3400 Livingston St., Washington, D.C. 20015

[21] Appl. No.: 984,506

[22] Filed: Dec. 2, 1992

Related U.S. Application Data

[63] Continuation-in-part of Ser. No. 962,651, Oct. 19, 1992.

[51] Int. Cl.⁵ ............................................. A61B 17/32
[52] U.S. Cl. .................................. 606/170; 606/174; 606/167; 606/207
[58] Field of Search .................. 128/751, 754, 755; 604/22; 606/37, 39, 45, 46, 51, 52, 79, 167, 170, 171, 174, 205, 207

[56] References Cited

U.S. PATENT DOCUMENTS

| | | |
|---|---|---|
| 464,075 | 12/1891 | Krank . |
| 2,507,710 | 7/1949 | Grosso . |
| 3,742,957 | 7/1973 | White . |
| 3,840,015 | 10/1974 | Gain . |
| 4,499,899 | 2/1985 | Lyons, III . |
| 4,602,631 | 7/1986 | Funatsu . |
| 4,655,216 | 4/1987 | Tischer . |
| 4,669,471 | 1/1987 | Hayashi . |
| 4,712,545 | 12/1987 | Honkanen . |
| 4,763,669 | 8/1988 | Jaeger . |
| 4,827,929 | 5/1989 | Hodge . |
| 4,880,015 | 11/1989 | Nierman . |
| 4,896,678 | 1/1990 | Ogawa . |
| 4,904,130 | 2/1990 | Gormon . |
| 4,944,741 | 7/1990 | Hasson . |
| 4,950,273 | 8/1990 | Briggs . |
| 5,133,735 | 7/1992 | Slater et al. . |
| 5,133,736 | 7/1992 | Bales. Jr. et al. . |
| 5,174,300 | 12/1992 | Bales et al. ........................... 606/170 |

Primary Examiner—C. Fred Rosenbaum
Assistant Examiner—N. Kent Gring
Attorney, Agent, or Firm—Wigman, Cohen, Leitner & Myers

[57] ABSTRACT

A laparoscopic surgical instrument is disclosed. The instrument generally comprises an elongated hollow shaft having at one end a pair of scissors and at the opposite end a pair of handles to control the scissors. The blades may be opened and closed when one handle is pivoted while the other handle is fixed. However, when both handles are rotated simultaneously the orientation of the blades relative to shaft changes so as to allow the blades to effectively cut or grasp curved tissues lying in a plurality of planes. Additionally, apparatus is provided to allow the blades to rotate about the longitudinal axis extending therethrough.

A depth gauge for laparoscopic scissors is also disclosed.

58 Claims, 6 Drawing Sheets

LAPAROSCOPIC INSTRUMENTS

CROSS REFERENCE TO RELATED APPLICATION

This application is a continuation-in-part of U.S. application Ser. No. 07/962,651 filed on Oct. 19, 1992 now pending.

FIELD OF THE INVENTION

The present invention relates to surgical instruments, and more particularly to scissors and related devices adapted to be used during laparoscopic surgery.

BACKGROUND OF THE INVENTION

Laparoscopic surgery is a relatively new surgical method wherein the surgery is performed through several small incisions of an average length not exceeding ½", made in the patient usually in the abdomen. Because the need to make large incisions is avoided, both the operating and recovery time for the patient is significantly reduced, resulting in significantly less cost and physical trauma for the patient. For example, removing an inflamed gallbladder by traditional methods can cost about $10,000.00, require a 6" incision through the abdomen, and necessitate a four or five day stay in the hospital, followed by several weeks of painful recovery. Removal of a gallbladder using the laparoscopic method could easily permit the patient to return home the day of the surgery and result in a complete recovery in a few days.

Typically, laparoscopic surgery requires two or more small incisions, one of which is used to insert a laparoscope, a viewing instrument which allows the surgeon to see the patient's internal organs, or, alternatively, a specially designed camera through which images are transmitted to a nearby video screen. Use of a camera allows the procedure to be viewed by several surgical personnel simultaneously and to be recorded on video tape. One or more additional incisions are required so that other miniaturized surgical instruments such as cutting, grasping, suturing, and stapling devices can be used, if required. These instruments must be long and narrow to pass through the small incision and reach the appropriate organ located within the body cavity. Moreover, because these devices are difficult to sterilize, they usually must be disposable. Finally, the laparoscopic instruments should be constructed with a minimum number of small parts due to the risk of such parts breaking off and lodging in the patient's body.

The incisions are usually made with a trocar, a pointed instrument which punctures the abdominal wall and positions a tube or cannula in the abdominal wall so that the laparoscope or other instruments may be passed therethrough.

Surgical scissors, per se, designed specifically for laparoscopic surgery are known in the art, as is shown in U.S. Pat. No. 5,133,736 to Bales Jr. et al.

A key disadvantage of the Bales, Jr. device in particular, and the prior art in general, is that the cutting plane of the blades is fixed relative to the shaft of the instrument thereby limiting the maneuverability and reach of the instrument. In laparoscopic surgery the shaft of the instrument is slidably received in a trocar tube so there is limited ability to orient the cutting plane and orientation of the blades of the conventional instruments. Conventional laparoscopic scissors are effective at cutting tissue in planes passing through the axis of the instrument shaft. However, most organs and tissue in the human body are curved and oriented along a multiplicity of planes. The prior art scissors have been found ineffective at reaching and cutting these tissues. Moreover, attempts to cut tissue without first orienting the cutting plane of the blades perpendicular to the tissue has often resulted in peripheral damage to adjacent arteries and other vital structures.

Hence, there is a strong need in the art for a laparoscopic surgical instrument having scissors, tweezers, forceps or the like which can be easily oriented into various planes to cut or grip the targeted tissue.

U.S. Pat. No. 4,763,669 to Jaeger discloses a surgical instrument having an adjustable angle of operation. This instrument, designed for obtaining biopsies and the like, is not suitable for laparoscopic surgery as it requires a two-handed operation. During typical laparoscopic surgery, the surgeon will simultaneously use one hand to operate a gripping device and the other hand to operate a cutting device. Hence, there is a need for such instruments wherein the scissors or the like can be operated and reoriented with the same hand. Another disadvantage with the Jaeger device is that the angle adjustment takes place only in a single plane, namely, the plane in which the grippers open and close.

Another problem frequently encountered during laparoscopic surgery stems from the fact that the surgeon cannot directly see the organ or tissue which is being cut, but rather must view the subject matter through a single lens scope or on a video screen. Since the image being viewed is two-dimensional, it is difficult to gauge the depth of cut being made.

Accordingly, there is a need for a scissors (or other elements) which can be used in laparoscopic surgery in a manner to help the surgeon ascertain the depth of cut being made.

SUMMARY AND ADVANTAGES OF THE INVENTION

The present invention is directed to a laparoscopic surgical instrument generally comprising an elongated hollow shaft having at one end a pair of scissors, and at the opposite end a housing. Rotatably mounted within the housing are a pair of handles which operate the scissors. Connection between the scissors and handles is accomplished by means of a specially designed linkage assembly which allows each blade to be independently controlled by a separate handle. In all embodiments of the invention, this linkage assembly allows the blades to be opened and closed as with conventional scissors when one handle is pivoted while the other handle is fixed. More importantly, however, when both handles are pivoted together, the angular orientation of the closed blades changes with respect to the longitudinal axis of shaft. Accordingly, the blades can not only be opened and closed in a conventional manner, but also can be pivoted upwardly or downwardly or sideways as a unit and then opened and closed to provide cutting or gripping action along an arcuate path. Moreover, both the opening and closing action and the pivoting of the blades can be effected with the same hand. This is particularly advantageous since the surgeon typically uses his/her other hand to operate a second laparoscopic instrument.

In the first embodiment of the invention, the pivoting of the blades takes place along the same plane in which the blades open and close.

In the second embodiment of the invention, the pivoting of the blades takes place along a plane generally perpendicular to the plane in which the blades open and close.

In the third embodiment of the invention, the pivoting of the blades takes place along a multiplicity of planes. This is accomplished by the addition of apparatus to rotate the scissors about it's longitudinal axis. In particular, the distal section includes two rotatably coupled sub-sections. Hence, the scissors of the third embodiment are adapted to move independently in three different ways: (1) to open and close in the manner of conventional scissors, (2) to pivot about a hinge, and (3) to rotate about its longitudinal axis.

With all embodiments, tweezer-like grippers or forceps may be substituted for the scissor blades. The same unique pivoting range is obtained with the grippers and forceps as is achieved with the scissors.

Additionally, the devices are preferably constructed of disposable materials. To aid the surgeon in gauging the depth of cut, a particular problem with laparoscopic surgery, a plurality of colored stripes are printed on the surface of the cutting blades.

It is a primary advantage of the laparoscope instrument of the present invention that the surgeon have increased versatility and manipulability over conventional surgical devices.

A more particular advantage of the laparoscope instrument of the present invention is the fact that the surgeon can adjust the angle of the blades as a unit with the same hand that is used for opening and closing the blades. Hence, the surgeon's other hand is free to operate a second laparoscopic instrument.

Still another advantage of the laparoscopic scissors of the present invention is the inclusion of a locking mechanism to fix the angle of the scissors as desired.

Yet another advantage of the laparoscopic scissors of the present invention is the inclusion of a depth gauge printed on the scissor blades to help the surgeon determine the depth of the cut being made.

With the foregoing and other advantages and features of the invention that will become hereinafter apparent, the nature of the invention may be more clearly understood by reference to the following detailed description of the invention, the appended claims and to the several views illustrated in the drawings.

DETAILED DESCRIPTION OF THE INVENTION EMBODIMENTS

Figures 1, 2:
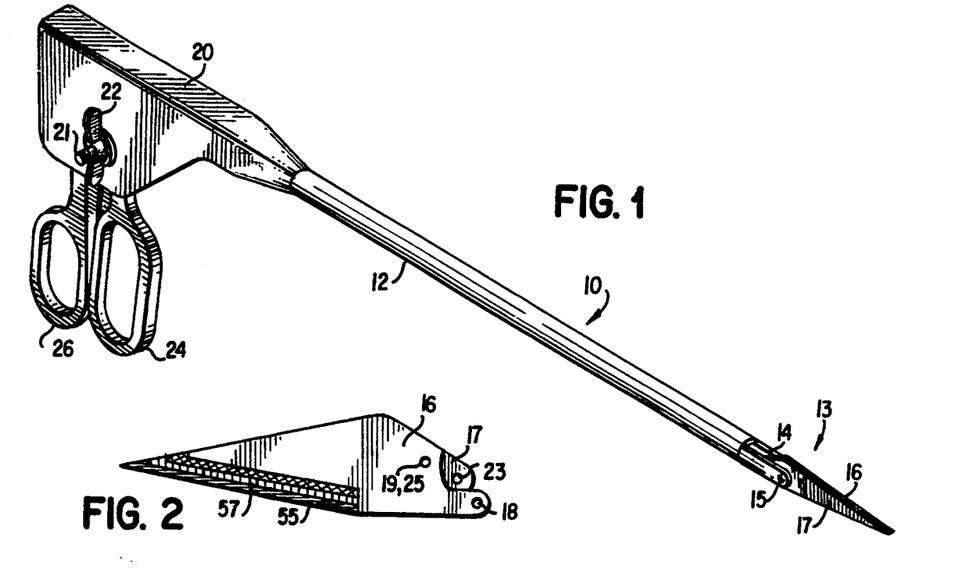
FIG. 1 is a perspective view of the first embodiment of the present invention.
FIG. 2 is a side elevational view of a pair of cutting blades of the present invention shown lined for color.
Figure 3:
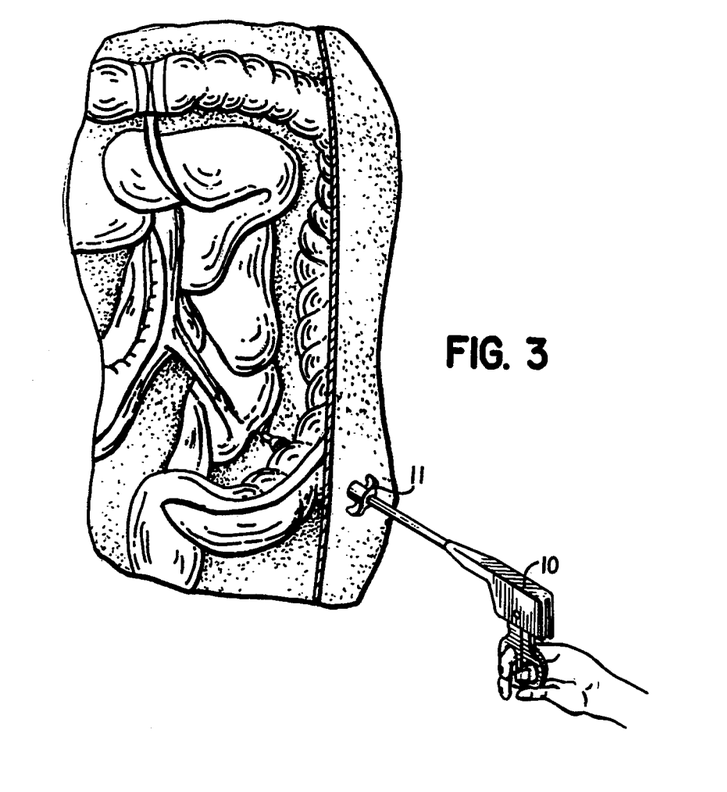
FIG. 3 is an environmental view of the laparoscopic scissors of the present invention shown in use during a typical laparoscopic surgical procedure.

Referring now in detail to the drawings wherein like parts are designated by like reference numerals throughout, there is illustrated in FIG. 1 a perspective view of a laparoscopic surgical instrument made in accordance with the first embodiment of the present invention and which is designated generally by reference numeral 10. As shown in FIG. 3, the instrument is adapted to be inserted into the abdomen of the patient via a trocar 11.

Instrument 10 generally comprises an elongated hollow shaft 12 having rotatably affixed thereto at its distal end an implement 13 which, in the embodiment shown, is a pair of scissors. Alternatively, implement 13 may comprise tweezers, forceps (FIG. 15) or the like. Shaft 12 terminates at a clevis 14 and the implement 13 is pivotably positioned and secured within the clevis 14 by pivot pin 15. In the embodiment shown, implement 13 comprises a pair of scissor blades 16, 17, each having a pair of holes 18, 19 and 23, 25 (FIG. 2). Holes 19, 25 of blades 16, 17 are adapted to receive pin 15 therethrough. Holes 18, 23 are used to provide the operational characteristics of the blades, as will be discussed hereinafter.

Figures 4, 5, 6, 6A, 6B, 7, 8:
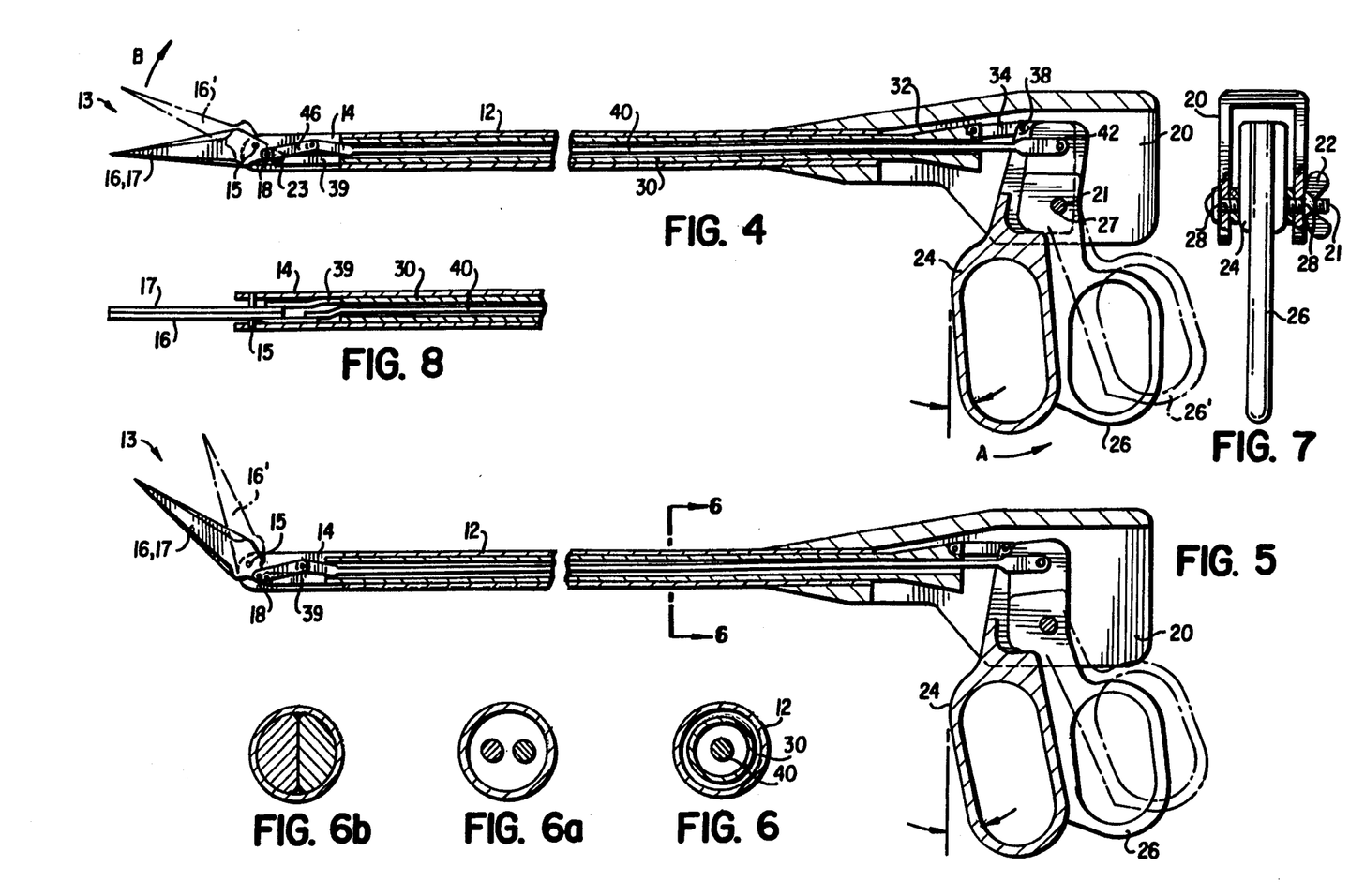
FIG. 4 is a side elevational view, partly in section, of the first embodiment of the present invention shown with the blades in a generally horizontal position.
FIG. 5 is a side elevational view, partly in section, of the first embodiment of the present invention shown with the blades angled upwardly.
FIG. 6 is a cross-sectional view taken along line 6—6 of FIG. 5.
FIG. 6a is a first alternative linkage assembly to that shown in FIG. 6.
FIG. 6b is a second alternative linkage assembly to that shown in FIG. 6.
FIG. 7 is a rear elevational view of the present invention.
FIG. 8 is a fragmentary top view partly in section, of the distal end of the laparoscopic scissors of the present invention.

At its proximal end, shaft 12 is secured to a housing 20. Pivotally mounted within the housing 20 are a pair of handles 24, 26 which operate the pivoting action of the blades 16, 17. The handles 24, 26 are rotatably secured to the housing 20 by a bolt 21 and wing nut 22 which can be removed to disassemble the handles for cleaning or the like (FIG. 7). As discussed hereinafter, wing nut 22 also functions to fix the angular orientation one blade with respect to the shaft.

More particularly, and with reference to FIGS. 4–8, handle 24 is provided with an opening sufficiently large for two fingers whereas handle 26 is provided with a smaller opening sufficient to receive a thumb. This arrangement allows the handles to be manipulated in the manner of conventional scissors. The handles 24, 26 are preferably constructed of a molded plastic or other electrically insulating or non-conductive material. Each handle is provided with an aperture 27 by which it is pivotably mounted to the housing. Housing 20 is also constructed of a molded plastic or a similar electrically insulating material and includes a pair of spaced holes 28 which are axially aligned with holes 27. Bolt 21 passes through apertures 27 in the handles and holes 28 in the housing (FIG. 7) so as to permit pivoting each handle member with respect to each other and to housing 20. Wing nut 22 is attached to bolt 21 to secure the handles to the housing. Appropriate spacers, bushings, or washers are also added. Preferably an indexing washer set, such as the type frequently employed with bicycle gears and hand tools is used so that the handle 24 can be indexed as it is pivoted.

The operational relationship between the handles 24, 26 and the implement 13 is preferably accomplished by means of an elongated tube member 30 and a rod member 40. Tubular member 30 is slidably positioned within hollow shaft 12 to operatively connect the finger handle 24 to the "fixed" blade 17 of the scissors implement 13. Member 30 is connected at its proximal end 32 to handle 24 by a linkage 34 which is pivotably attached to the uppermost portion 38 of the handle 24 and to the proximal end of member 30 by pins, screws or the like. The distal end of tubular member 30 includes a linkage extension 39 which is pivotably connected to aperture 23 of blade 17 as by a screw. With this arrangement, rotation of handle 24 in the direction of arrow A (FIG. 4) urges tubular member 30 forward thereby urging blade 17 to rotate in an upward or clockwise direction about pin 15.

Rod 40, which connects the thumb handle 26 to blade 16, is slidably received inside tubular member 30. At its proximal end, rod 40 is pivotably connected to handle 26 at flattened portion 42. At its distal end, linkage 46 pivotably connects the rod to the aperture 18 of blade 16. With this arrangement, rotation of handle 26 in the counterclockwise direction (arrow A, FIG. 4) to position 26' urges rod 40 forward thereby urging blade 16 to rotate in a clockwise direction (arrow B, FIG. 4) to position 16'.

Alternatively in lieu of the above-described rod and tube arrangement, a pair of generally parallel rods (FIG. 6a) which passes through shaft 12 maybe employed. Another variation to the rod and tube linkage assembly is a pair of solid members, each having a generally semi-circular cross section.

In order to fix the finger handle 24 while the thumb handle 26 is rotated, wing nut 22 is tightened. Tightening the wing nut 22 causes the walls of housing 20 to bend inward so as to grip the handle by 24 as best viewed in FIG. 7. However, because the handles are constructed of a more rigid material than the housing, the tightening does not prevent handle 26 from pivoting relative to the other handle and housing 20. When handle 26 is pivoted with handle 24 fixed, the blades open and close in the manner of conventional scissors. However, when the both handles 24, 26 are rotated as a unit, the angle of the blades changes with respect to the longitudinal axis of shaft 12.

Figures 13, 14, 15:
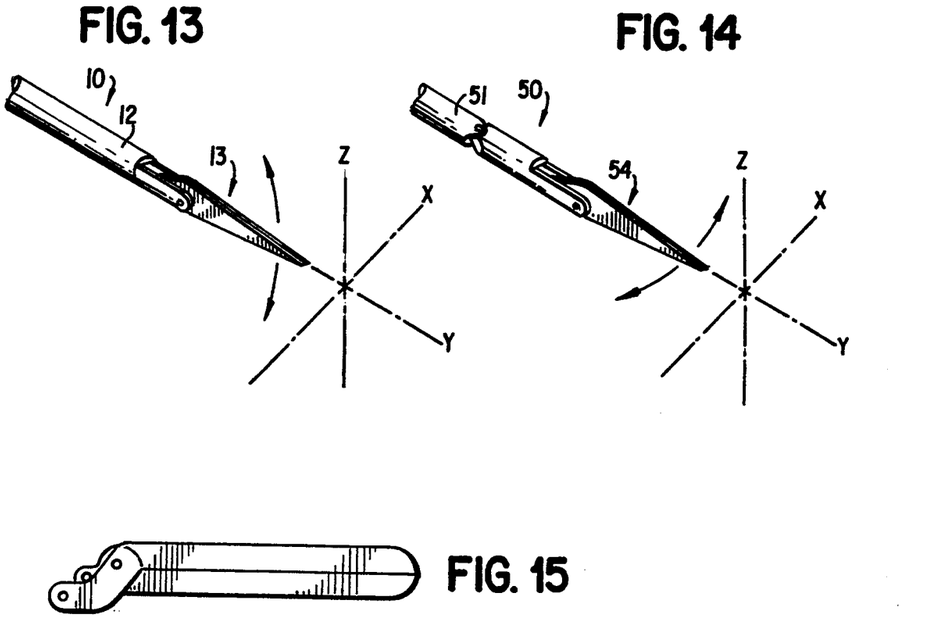
FIG. 13 is a perspective view of the distal end of the first embodiment of the present invention shown with the three dimensional axes.
FIG. 14 is a perspective view of the distal end of the second embodiment of the present invention shown with the three dimensional axes.
FIG. 15 is a side elevation view of forceps which may be employed with the first embodiment of the present invention.

As best illustrated in FIG. 13, such angular reorientation of the implement 13 occurs in the Y-Z plane in the directions shown by the arrows with the longitudinal axis of shaft 12 oriented parallel to line Y.

Figure 16:
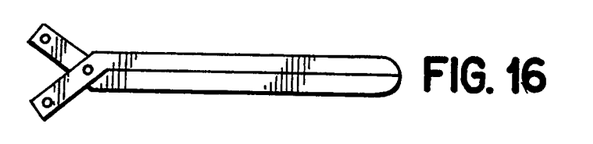
FIG. 16 is a side elevation view of forceps which may be employed with the second embodiment of the present invention.

The second embodiment 50 of the present invention, as shown by the arrows in FIG. 14, allows the implement to pivot in the X-Y plane. Hence, the implement is pivotable along a plane perpendicular to the plane in which the blades open and close. As shown in FIGS. 9 through 12, the second embodiment 50, like the first embodiment, generally comprises an elongated hollow shaft 52 having at its distal end a scissors 54 or a similar implement and at its proximal end a housing 60 having rotatably mounted thereto a pair of handles 56, 58. Movement of the thumb handle 56 with the finger handle 58 fixed causes the scissors 54 to open and close in the manner of conventional scissors. As with the first embodiment, forceps (FIG. 16) or tweezers may be employed. Movement of the finger handle 58 causes the distal end 53 of shaft 52 which carries implement 54 to pivot about hinge 51 thereby allowing angular reorientation of the implement.

More particularly, both handles are pivotally mounted to the housing by bolt 65. Thumb handle 56 is operatively connected to scissors 54 by a flexible cable 62. The cable is connected to the handle 56 at aperture 63, passes through the shaft 52, and is attached at its opposite end to a pair of linkage members 64. Each linkage member is connected to a respective blade of scissors 54 which are biased to an open position by a torsion spring (not shown) arranged along the pivot axis of the blades or by other resilient biasing mechanism. With this arrangement, pivoting of handle 56 in the direction of arrow C relaxes tension in cable 62 thereby allowing the biasing means to urge the blades to open their positions. Pivoting of handle 56 in the opposite direction from that shown by arrow C exerts tension in the cable thereby pulling the scissor blades 54 closed against the force of the biasing means.

Finger handle 58, which controls the pivoting of the distal tip 53 of shaft 52 about the hinge 51 is operatively connected to the hinge by a rod 66. At its proximal end, rod 66 is pivotably connected to handle 58 at aperture 68. The rod passes through shaft 52, generally parallel to cable 62 and is pivotably mounted at its distal end to stem 70. Pivoting of the finger handle 58 in the direction of arrow C will urge rod 66 forward thereby urging the tip 53 to rotate in the position illustrated in FIG. 11a. Similarly, pivoting finger handle 58 in the direction opposite arrow C will pull rod 66 backwards thereby urging the tip 53 to rotate in the position illustrated in FIG. 11b.

In lieu of rod 66, a pair of cables may be employed to rotate the distal end 53 about hinge 51. The specifics of this two-cable arrangement are disclosed below in connection with the third embodiment of the present invention.

Because the surgeon is viewing the procedure on a video monitor and does not have the advantage of a three-dimensional view of the subject matter being cut, a plurality of colored stripes 57 are preferably printed on the surface of the blades 16, 17 (FIG. 2) adjacent to the forwardly extending cutting edge 55. Both faces of each blade are preferably provided with a plurality of colored stripes 57 along the tip and cutting edge of the blades. The stripes 57 assist the surgeon in determining the depth of the cut being made. For optimal visibility, the colors of the stripes should contrast with the colors of tissue and fluids in the human body. For example, the colors blue, green, black and white, which are not typically found in the human body are preferable over the colors red, yellow, or brown, which are found throughout the human body. Also, to improve the visibility of the stripes they may comprise a photoluminescent coating.

The third embodiment of the present invention is illustrated in FIGS. 17 through 26 and is structurally similar to the second embodiment but further includes apparatus to rotate the scissors or similar implement about it's longitudinal axis, in addition to pivoting in the manner of the first and second embodiments. This additional range of movement allows the third embodiment implement to pivot in both the Y-Z plane and the X-Y plane at the discretion of the surgeon. The third embodiment, like the first and second embodiments, generally comprises an elongated hollow shaft substantially identical to shaft 52 of the first and second embodiment. The shaft has a proximal section 152 and a distal section generally designated as 153 pivotably mounted thereto by a hinge 170 (FIGS. 21 through 24). Distal section 153 carries scissors 154 or a similar implement in the same manner as the first and second embodiments. Housing 160 receives the proximal end of section 152 (FIG. 20) and includes handles 156, 158 which are rotatably mounted to the housing 160. Handle 156 is preferably thumb operated and is connected to scissors 154 by a flexible cable 162. Handle 158 is preferably operated by one or more fingers. Parts 163, 165 and 168 of the third embodiment are identical in structure and function to parts 63, 65, and 68 of the second embodiment. As with the first and second embodiments, movement of the thumb handle 156 with the finger handle 158 being fixed causes the scissors 154 to open and close in the manner of conventional scissors. Finger handle 158, which controls the pivoting of the distal section 153 of the shaft, is operatively connected to section 153 by a rod 166. Movement of the finger handle 158 causes the distal section 153 which carries implement 154 to pivot about hinge 170 thereby allowing angular reorientation of the implement. As with the first and second embodiments, both handles are pivotally mounted to the housing by bolt 65. The specific arrangements and characteristics of the cable 162 and rod 166 are substantially similar to the cable 62 and rod 66 of the second embodiment.

Figures 12, 25, 26:
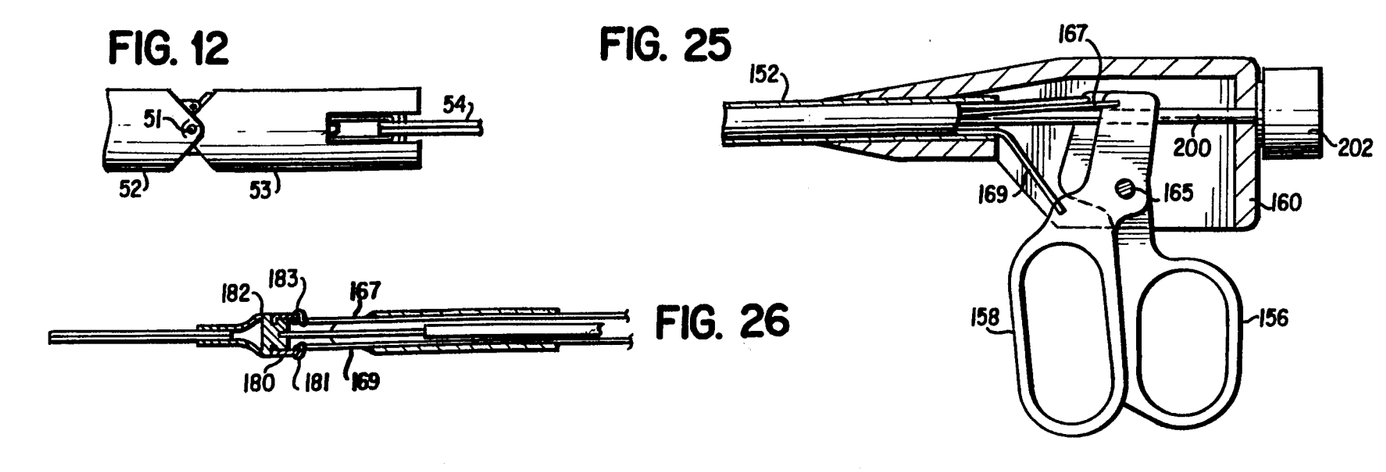
FIG. 12 is a top plan view of the distal end of the second embodiment of the present invention
FIG. 25 is a side elevational view, partly in section, of the proximal end of the third embodiment of the present invention shown with a linkage assembly modified from that illustrated in FIG. 20.
FIG. 26 is a top plan view of the distal end of the embodiment shown in FIG. 25.
Figure 24:
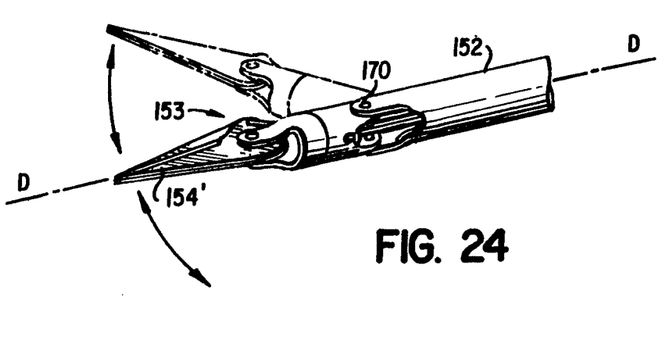
FIG. 24 is the view of FIG. 23 wherein the scissors are rotated 90° about its longitudinal axis from the position shown in FIG. 23.

Referring to FIGS. 24–26 alternatively, in lieu of rod 166, a pair of cables 167, 169 is employed to rotate distal tip 153 about hinge 170. In FIG. 25, cable 167 at its proximal end is connected to the top portion of handle 158 and cable 169 at its proximal end is connected to the middle portion of handle 158. Cable 167 at its distal end is connected to section 180 by a knot or weld 181 and cable 169 is mounted to the opposite side of section 180 by a similar connection 183. Hence, pulling handle 158 causes tension in cable 169 and slack in cable 167 thereby urging distal tip 153 in a counterclockwise direction. Similarily, pushing handle 158 forward causes tension in cable 167 and slack in cable 169 thereby urging distal tip 153 in a clockwise direction.

Figure 17:
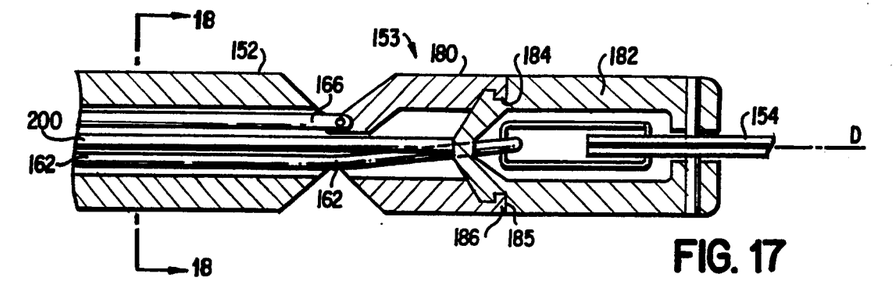
FIG. 17 is a top sectional view of the distal end of the third embodiment of the present invention.

To allow the scissors 154 to rotate about its longitudinal axis D, distal section 153 is comprised of two sub-sections, 180, 182, rotatably coupled to one another (FIG. 17). In particular, section 182 is preferably comprised of a cylindrical body with a generally conical wall 184 mounted to the proximal end thereof and integrally formed therewith. An annular recess 186 is provided in conical wall 184 and is integrally formed therewith. Opposing section 180 is a generally cylindrical body wherein the distal edge is provided with an upturned annular rib 185 adapted to mate with the annular recess 186 of the opposing section. This arrangement allows section 182 to rotate with respect to section 180. Alternatively, sub-sections 180, 182 may be shaped as illustrated in FIG. 26.

Figures 9, 10, 11A, 11B, 18:
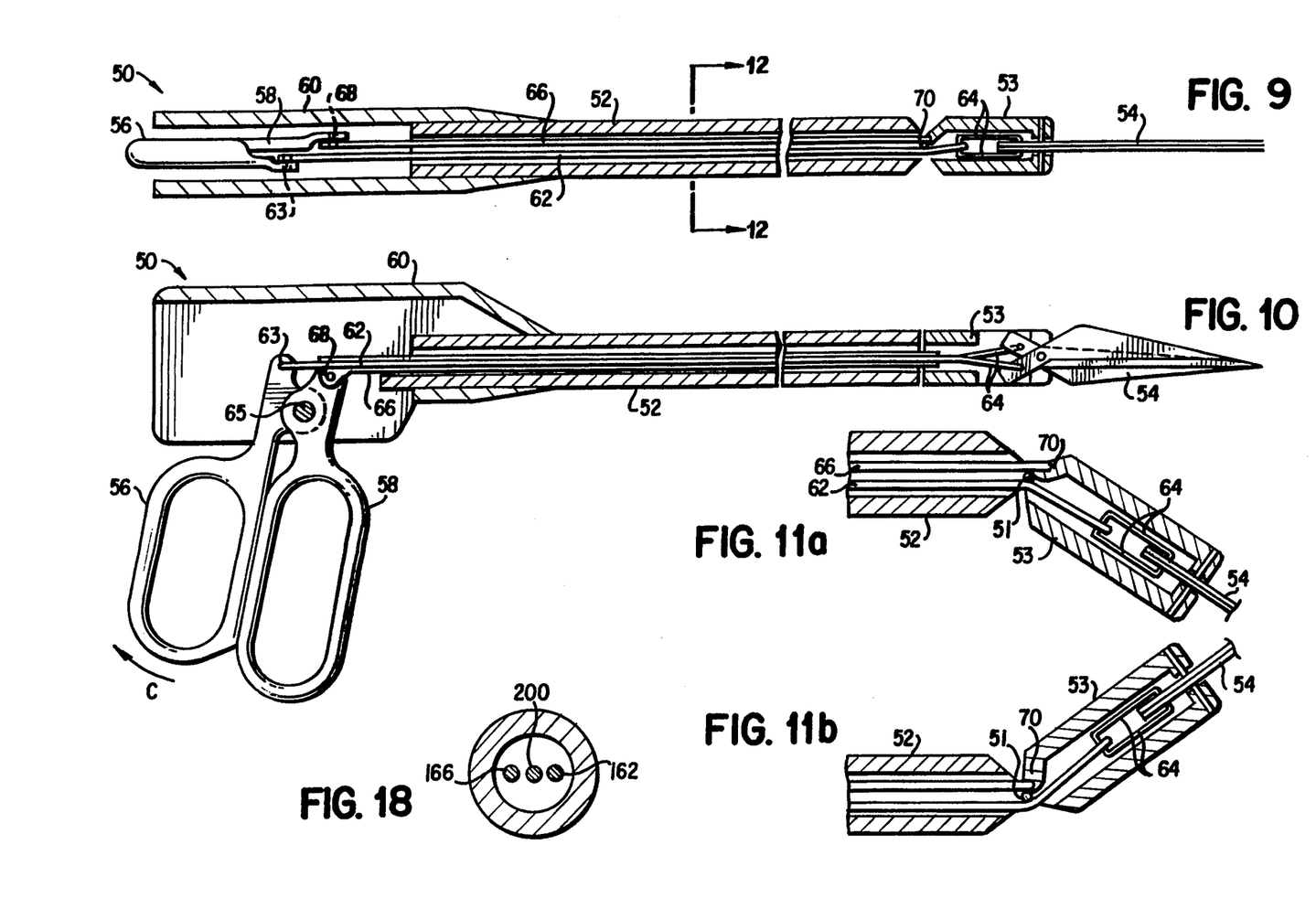
FIG. 9 is a top view, partly in section, of the second embodiment of the present invention.
FIG. 10 is a side elevational view, partly in section, of the second embodiment of the present invention.
FIG. 11a is a top sectional view of the distal end of the second embodiment of the present invention shown in a clockwise angled position.
FIG. 11b is a top sectional view of the distal end of the second embodiment of the present invention shown in a counterclockwise angled position.
FIG. 18 is a cross-sectional view taken along line 18—18 of FIG. 17.
Figure 19:
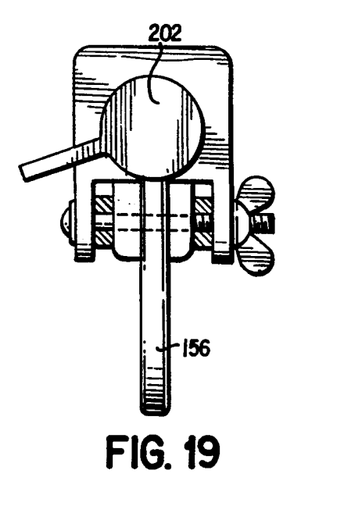
FIG. 19 is a rear elevational view of the third embodiment of the present invention.
Figure 20A:
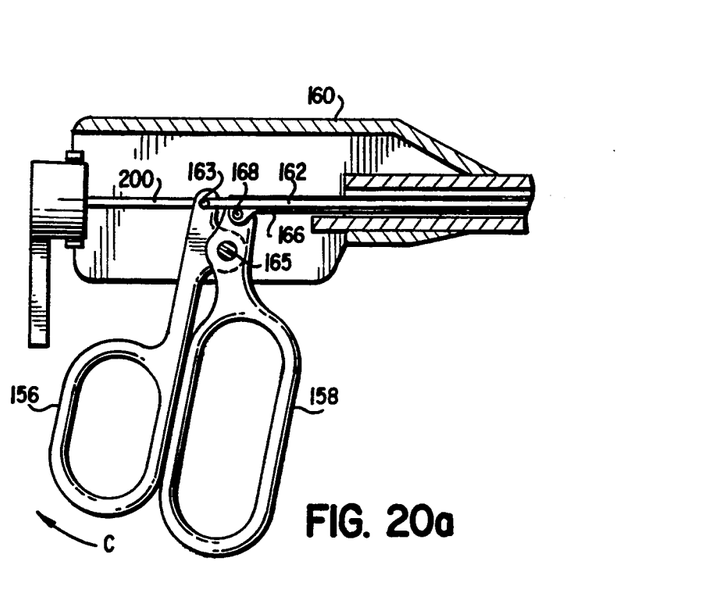
FIG. 20a is a side elevational view, partly in section of the proximal end of the third embodiment of the present invention.
Figure 20B:
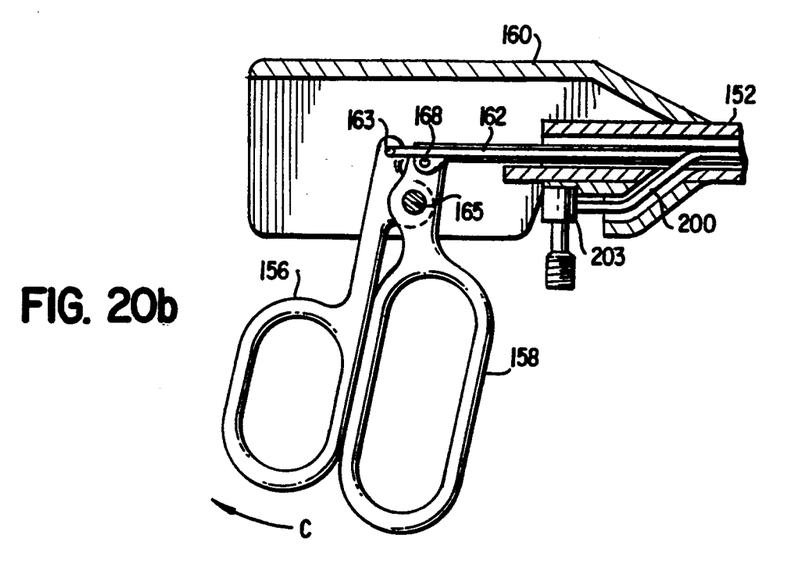
FIG. 20b is a view of FIG. 20a shown with the knob distal to the handles.

Rotation is controlled by a cable 200 connected at its distal end to conical wall 184. Cable 200 is preferably a Bowden-type cable, that is, a wire made of spring steel enclosed in a helical casing and used to transmit radial motion over distances, around corners or the like Cable 200 extends through the hollow shaft 152 intermediate rod 166 and cable 162 (FIG. 18). Or, with respect to the two-cable embodiment, intermediate cables 167, 169 (FIG. 26). At its proximal end, cable 200 is attached to knob 202 which, in turn, is rotatably mounted to housing 160 (FIGS. 19 & 20a). Mounting of knob 202 preferably includes an indexing or ratcheting device. Alternatively, a knob 203 may be mounted distal to handles 156, 158 (FIG. 20b) so that it may be controlled by the user's finger. At its distal end, cable 200 is fixed to section 182, by welding, or brazing or the like. With this arrangement, rotation of knob 202 twists cable 200 which, in turn, causes section 182 to rotate. It is a particular feature of the present invention that the above-identified rotation may be accomplished even when the distal end 153 is bent about hinge 170 shown in FIGS. 21 through 24. This is so because cable 200, though flexible, is capable of translating torque even when bent.

Figure 21:
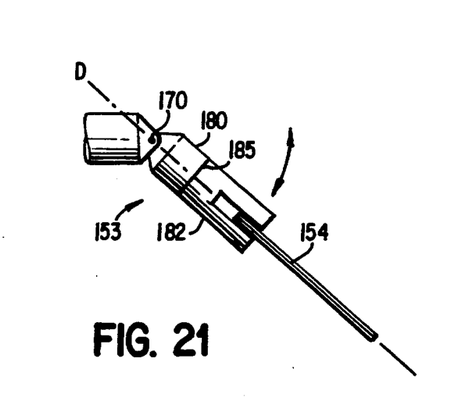
FIG. 21 is a top plan view of the distal end of the third embodiment of the present invention shown in a clockwise angled position.
Figure 23:
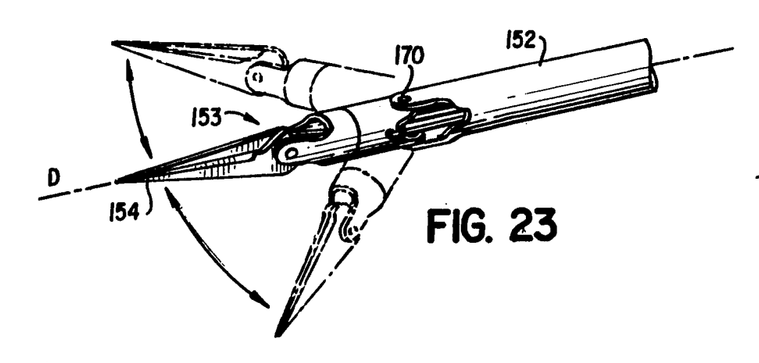
FIG. 23 is a perspective view of the distal end of the third embodiment of the present invention.

FIGS. 21 and 23 show the distal end of the third embodiment with the scissors 154 positioned to open and close in a plane perpendicular to the plane in which the distal section 153 pivots about hinge 170. In this position the device may be manipulated in the same manner as the second embodiment of the present invention (i.e., in the X-Y plane).

Figure 22:
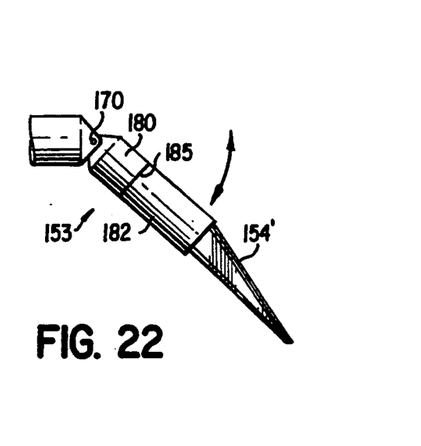
FIG. 22 is the view of FIG. 21 wherein the scissors are rotated 90° about its longitudinal axis from the position shown in FIG. 21.

FIGS. 22 and 24 show the scissors 154' rotated about its longitudinal axis D approximately 90° from the position shown in FIGS. 21 and 23. The scissors 154' are therefore positioned to open and close in the same plane in which the distal section 153 pivots about hinge 170. In this position, the device may be manipulated in the same manner as the first embodiment of the present invention (i.e., in the Y-Z plane).

To take advantage of the additional range of motion provided by the third embodiment, the surgeon need only rotate handles 156, 158 approximately 90° about the longitudinal axis of the shaft. Then, using his/her thumb from the same hand which control handles 156, 158, rotate knob 202 approximately 90° so as to cause the scissors 154 to rotate about its longitudinal axis.

In summary, the scissors (or similar implement) 154 of the third embodiment are adapted to move independently in three different ways: (1) to open and close in the manner of conventional scissors, (2) to pivot about hinge 170, and (3) to rotate about its longitudinal axis. All three types of movement may be controlled with one hand.

In use and operation, one or more trocars are inserted into the body of the patient. A laparoscope is passed through at least one of the trocars to allow the surgeon to view the organs. Additionally, $CO_2$ is insuflated into the abdominal cavity in the manner known by those skilled in the art. The surgeon then selects the appropriate embodiment of the present invention based on the location and orientation of the targeted tissue. The instrument is then passed through the trocar 11 (FIG. 3) and the cutting plane and orientation of the blades is adjusted by rotating the finger handle. The finger handle may then be locked in position by tightening the wing-nut or, if desired, the wing-nut may remain loose to enable the surgeon to adjust the orientation of the blades as he cuts.

Although certain preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A surgical instrument, especially for use in laparoscopic surgery comprising:
   an elongated shaft bearing distal and proximal ends;
   a surgical implement pivotably mounted to the distal end of said shaft, said surgical implement comprising a pair of members movable with respect to one another for performing an operative step;
   first and second handles pivotally mounted to the proximal end of the shaft, said handles being pivotally movable together relative to the shaft and pivotable relative to each other; said handles being operatively connected to said surgical implement such that pivotable movement of both of said handles together in one direction simultaneously pivots both of said members of said implement together in one direction relative to the shaft, and pivotable movement of said first handle relative to said second handle moves the members of the surgical implement relative to each other to perform said operative step.

2. The instrument of claim 1, wherein said surgical implement comprises scissors and said operative step is a cutting step.

3. The instrument of claim 2 wherein said scissors comprise a pair of blades, at least one blade having indicia thereon for indicating the depth of cut being made.

4. The instrument of claim 3, wherein said indicia comprise a plurality of stripes of two or more contrasting colors.

5. The instrument of claim 4 wherein the stripes are located adjacent the cutting edge of said blade.

6. The instrument of claim 4 wherein the colors of said stripes are selected from the group consisting of blue, green, black and white.

7. The instrument of claim 4 wherein the colors of said stripes are photo luminescent.

8. The instrument of claim 1, wherein the pair of members of the surgical implement are movable with respect to one another in a first plane and the surgical implement is pivotable relative to the distal end of the shaft in said first plane.

9. The instrument of claim 8 wherein said surgical implement is a cutting instrument.

10. The instrument of claim 9 wherein said cutting instrument is a pair of scissors.

11. The instrument of claim 8 wherein said surgical implement is a grasping instrument.

12. The instrument of claim 11 wherein said grasping instrument is a pair of forceps.

13. The instrument of claim 1, wherein the pair of members of the surgical implement are movable with respect to one another in a first plane and the surgical implement is pivotable relative to the distal end of the shaft in a second plane substantially perpendicular to said first plane.

14. The instrument of claim 13 wherein said surgical implement is a cutting instrument.

15. The instrument of claim 14 wherein said cutting instrument is a pair of scissors.

16. The instrument of claim 13 wherein said surgical implement is a grasping instrument.

17. The instrument of claim 16 wherein said grasping instrument is a pair of forceps.

18. The instrument of claim 1, and wherein said implement is pivotable about the longitudinal axis extending therethrough.

19. The instrument of claim 18 wherein said surgical implement is a grasping instrument.

20. The instrument of claim 19 wherein said grasping instrument is a pair of forceps.

21. The instrument of claim 18 wherein said distal end comprises a first section and a second section in proximal relation to said first section, said first section rotatably coupled to said second section.

22. The instrument of claim 18 further including a cable having distal and proximal ends, said distal end operatively connected to said element and said proximal end operatively connected to a knob.

23. The instrument of claim 18, wherein said surgical implement comprises scissors and said operative step is a cutting step.

24. The instrument of claim 18 wherein said scissors comprise a pair of blades, at least one blade having indicia thereon for indicating the depth of cut being made.

25. A surgical instrument, especially useful for laparoscopic surgery comprising:
   a first tubular member having distal and proximal ends;
   a second tubular member, having distal and proximal ends, the proximal end of the second tubular member being pivotably mounted to the distal end of said first tubular member by a hinge;

a third tubular member, having distal and proximal ends, the proximal end of the third tubular member being rotatably coupled to the distal end of said second tubular member;

a surgical implement pivotably mounted to the distal end of said third tubular member, said surgical implement comprising a pair of members movable with respect to one another for performing an operative step;

first and second handles mounted at the proximal end of said first tubular member adapted to receive the user's fingers each of said handles being independently movable with respect to said first tubular member;

means extending through said first tubular member for pivoting said second tubular member relative to said first tubular member, about said hinge;

a first cable which is secured at one end to the first of said handles and at the other end to said implement; and, a second cable secured at one end to said rotatable member and at its other end to said third tubular member.

26. The instrument of claim 25 further including a housing mounted at the proximal end of said first tubular member.

27. The instrument of claim 26 wherein said handles are mounted to said housing.

28. The instrument of claim 27 further including a member mounted to said housing for rotating said third tubular member.

29. The instrument of claim 25 further including a member mounted near said handles for rotating said third tubular member.

30. The instrument of claim 29 wherein said rotatable member is a lever.

31. The instrument of claim 29 wherein said rotatable member is a knob.

32. The instrument of claim 25 wherein said pivoting means comprises a rod secured at one end to the second of said handles and at its opposite end to said second tubular member.

33. The instrument of claim 25 wherein said pivoting means comprises a third and fourth cable, said third cable connected at one end to the second of said handles and at the opposite end to a first side of said second tubular member, said fourth cable connected at one end to the second of said handles, spaced from the connection point of the third cable, and at the opposite end to said a side of second tubular member opposite said first side.

34. The instrument of claim 25 wherein said implement is a scissors.

35. The instrument of claim 25 wherein said second cable is a Bowden cable.

36. A surgical instrument, especially useful for laparoscopic surgery comprising:

a first tubular shaft having a distal end and a proximal end, said distal end adapted to be inserted within a patient's body, and said proximal end adapted to be located outside a patient's body;

an implement pivotably mounted to the distal end of said shaft, said implement having a pair of members adapted to open and close in a scissor-like fashion;

a pair of handles pivotably mounted to the proximal end of said shaft comprising a first handle adapted to receive the user's fingers and a second handle adapted to receive the user's thumb, both of said handles being independently movable with respect to said first shaft;

a pair of reciprocally movable connecting elements extending through said first tubular shaft, connected at their proximal ends to said handles and at their distal ends to said implement;

a locking device which prevents movement of one of said handles while allowing movement of said other handle;

whereby when said first handle is locked, movement of said second handle causes said second implement member to move relative to said first implement member, and whereby moving both handles simultaneously causes both implement members to simultaneously change its pivot angle relative to the longitudinal axis of said shaft.

37. The instrument of claim 36 wherein the pair of members of the surgical implement are movable with respect to one another in a first plane and the surgical implement is pivotable relative to the distal end of the shaft in a second plane substantially perpendicular to said first plane.

38. The instrument of claim 37 wherein the tubular shaft comprises a hinged portion being pivoted at the distal end, said hinged portion being pivoted by the action of one of said handles to alter the cutting plane of said scissors.

39. The instrument of claim 36 wherein said implement comprises a pair of scissors.

40. The instrument of claim 36 wherein said implement comprises a pair of tweezers.

41. The instrument of claim 36 wherein said implement comprises a pair of forceps.

42. The instrument of claim 36 wherein the members of the surgical implement are movable with respect to one another in a first plane and the surgical implement is pivotable relative to the distal end of the shaft in said first plane.

43. A surgical instrument, especially useful for laparoscopic surgery, comprising:

an elongated tubular shaft having a distal end and a proximal end, said distal end adapted to be inserted within a patient's body;

a pair of scissors pivotally mounted to the distal end of said shaft, said scissors adapted to open and close within a first plane, and wherein the angle of said scissors relative to the longitudinal axis of said shaft is adjustable;

control apparatus mounted to the proximal end of said shaft for opening and closing said scissors and for adjusting the angle of said scissors relative to the longitudinal axis of said shaft; said control apparatus comprising a pair of handles, each being independently moveable with respect to each other, said scissors being operatively connected to said handles wherein movement of both of said handles together in one direction changes the angle of said scissors relative to the longitudinal axis of said shaft.

44. The instrument of claim 43, and wherein said scissors are rotatable about the longitudinal axis extending therethrough.

45. The surgical instrument of claim 4 wherein said scissors include a pair of cutting blades, at least one of said blades having indicia applied thereto for ascertaining the depth of penetration of said blade.

46. The surgical instrument of claim 43 further comprising a locking device for releasably-fixing one of said handles while permitting the other handle to operate said scissors.

47. A surgical instrument, especially for use in laparoscopic surgery comprising:
an elongated shaft bearing distal and proximal ends;
a surgical implement pivotably mounted to the distal end of said shaft, said surgical implement comprising a pair of members movable with respect to one another for performing an operative step;
first and second handles pivotally mounted to the proximal end of the shaft, said handles being pivotably movable together relative to the shaft and pivotable relative to each other; said handles being operatively connected to said surgical implement such that pivotable movement of both of said handles together in one direction simultaneously pivots the surgical implement relative to the shaft and pivotable movement of said first handle relative to said second handle moves the members of the surgical implement relative to each other to perform said operative step;
wherein said shaft comprises a first tubular member; means extending through said tubular member for operating said surgical implement comprising a first linkage member connecting the first handle to one member of the surgical implement, a second linkage member connecting the second handle to another member of the surgical implement.

48. The instrument of claim 47, wherein said second linkage member comprises a second tubular member reciprocally movable in said first tubular member and said first linkage member comprises a rod member reciprocally movable in said second tubular member.

49. The instrument of claim 47 wherein said means for operating said surgical implement comprises a pair of elongated rods which extend through said tubular member.

50. The instrument of claim 47 wherein said means for operating said surgical implement comprise a pair of elongated hemispherically shaped rods positioned in abutting relationship.

51. A surgical instrument, especially for use in laparoscopic surgery, comprising:
an elongated shaft bearing distal and proximal ends;
a pair of scissor-like members pivotably mounted to the distal end of said shaft by hinges, said members adapted to be opened and closed with respect to one another for performing an operative step; and means for opening and closing said members,
wherein said members may be movable together about said hinge relative to said shaft independent of the opened or closed position of said members; and
wherein said members may be substantially fully rotatable about the horizontal axis extending through said members.

52. The instrument of claim 51 wherein said implement is a scissors having a pair of blades which are moveable with respect to each other the tips of the scissors being simultaneously pivotable together and being simultaneously rotatable.

53. The instrument of claim 51 wherein said implement is a forceps having a pair of blades which are moveable with respect to each other the tips of the scissors being simultaneously pivotable together and being simultaneously rotatable.

54. The instrument of claim 51 wherein said implement is a tweezers having a pair of blades which are moveable with respect to each other the tips of the scissors being simultaneously pivotable together and being simultaneously rotatable.

55. The surgical instrument according to claim 51 wherein said elongated shaft and scissor-like members both being of a size enabling them to pass through a trocar cannula.

56. A surgical instrument, especially for use in laparoscopic surgery comprising:
an elongated shaft bearing distal and proximal ends said distal end comprising a first section and a second section in proximal relation to said first section, said first section rotatably coupled to said second section;
a surgical implement pivotably mounted to said first section, said surgical implement comprising a pair of members movable with respect to one another for performing an operative step;
first and second handles pivotally mounted to the proximal end of the shaft, said handles being pivotably movable relative to the shaft and to each other; said handles being operatively connected to said surgical implement such that simultaneous movement of said handles pivots the surgical implement relative to the shaft and movement of said first handle relative to said second handle moves the members of the surgical implement relative to each other to perform said operative step and wherein said implement is pivotable about the longitudinal axis extending therethrough;
said first section comprising:
a tubular body closed by distal and proximal side walls, said distal side wall defining an aperature through which said implement may protrude, said proximal side wall conically shaped and defining an annular recess
said second section comprising:
a tubular body having at its distal end an annular flange for engaging said annular recess of said first section.

57. A surgical instrument, especially for use in laparoscopic surgery, comprising:
an elongated shaft bearing distal and proximal ends;
a surgical implement pivotally mounted to the distal end of such shaft, such surgical implement comprising a pair of members movable with respect to one another for performing an operative step,
said elongated shaft and surgical implement both being of a size enabling them to pass through a trocar cannula;
first and second handles pivotally mounted to the proximal end of this shaft, said handles being pivotally movable together relative to the shaft and pivotable relative to each other;
said handles being operatively connected to said surgical implement such that pivotable movement of both of said handles together in one direction simultaneously pivots the surgical implement relative to the shaft, and pivotable movement of said first handle relative to said second handle moves the members of the surgical implement relative to each other to perform said operative step.

58. A surgical instrument, especially for use in laparoscopic surgery, comprising:
an elongated tubular shaft having a distal end and a proximal end, said distal end adapted to be inserted within a patient's body;

a pair of scissors pivotably mounted to the distal end of said shaft, said scissors adapted to open and close within a first plane, and wherein the angle of said scissors relative to the longitudinal axis of said shaft is adjustable, said elongated shaft and surgical instrument both being of a size enabling them to pass through a trocar cannula;

control apparatus mounted to the proximal end of said shaft for opening and closing said scissors and for adjusting the angle of said scissors relative to the longitudinal axis of said shaft;

said control apparatus comprising a pair of handles operatively connecting said scissors.

* * * * *